(12) United States Patent
Pettinato et al.

(10) Patent No.: US 12,356,982 B2
(45) Date of Patent: Jul. 15, 2025

(54) OXYGENATOR DEVICE

(71) Applicant: LIFELINE SCIENTIFIC, INC., Itasca, IL (US)

(72) Inventors: David Pettinato, Schaumburg, IL (US); Christopher P. Steinman, Sandy, UT (US); Alan K. Wu, Homewood, IL (US)

(73) Assignee: LIFELINE SCIENTIFIC, INC., Itasca, IL (US)

( * ) Notice: Subject to any disclaimer, the term of this patent is extended or adjusted under 35 U.S.C. 154(b) by 1752 days.

(21) Appl. No.: 16/353,188

(22) Filed: Mar. 14, 2019

(65) Prior Publication Data

US 2020/0288701 A1 Sep. 17, 2020

(51) Int. Cl.
| | |
|---|---|
| *A01N 1/143* | (2025.01) |
| *A01N 1/122* | (2025.01) |
| *A61M 1/14* | (2006.01) |
| *A61M 60/31* | (2021.01) |

(52) U.S. Cl.
CPC ............. *A01N 1/143* (2025.01); *A61M 60/31* (2021.01); *A01N 1/122* (2025.01); *A61M 1/14* (2013.01)

(58) Field of Classification Search
None
See application file for complete search history.

(56) References Cited

U.S. PATENT DOCUMENTS

| | | | |
|---|---|---|---|
| 3,892,628 A | 7/1975 | Thorne et al. | |
| 3,914,954 A * | 10/1975 | Doerig | A01N 1/165 435/284.1 |
| 4,186,565 A | 2/1980 | Toledo-Pereyra | |
| 5,051,352 A | 9/1991 | Martindale et al. | |
| 5,270,005 A | 12/1993 | Raible | |
| 5,322,500 A | 6/1994 | Johnson et al. | |
| 5,356,771 A | 10/1994 | O'Dell | |
| 5,368,555 A | 11/1994 | Sussman et al. | |
| 5,378,345 A | 1/1995 | Taylor et al. | |
| 5,494,822 A | 2/1996 | Sadri | |
| 5,586,438 A | 12/1996 | Fahy | |
| 6,046,046 A | 4/2000 | Hassanein | |
| 6,100,082 A | 8/2000 | Hassanein | |

(Continued)

FOREIGN PATENT DOCUMENTS

| | | | |
|---|---|---|---|
| CN | 109380213 | * | 2/2019 |
| CN | 109380213 A | | 2/2019 |

(Continued)

OTHER PUBLICATIONS

Fisher Scientific. Three-Prong Extension Clamps. Retrieved Mar. 5, 2023. https://web.archive.org/web/20161114114722/https://www.fishersci.com/us/en/products/19C8K6PQ/clamps-stands-supports.html (Year: 2016).*

(Continued)

*Primary Examiner* — Michael A Marcheschi
*Assistant Examiner* — Nathan G Esperon
(74) *Attorney, Agent, or Firm* — Oliff PLC

(57) ABSTRACT

Disclosed is an oxygenator device for oxygenating a perfusate solution to be perfused through an organ or tissue. The device includes an inlet configured to receive oxygen from an oxygen supply; and tubing connected to the inlet, the tubing including a plurality of holes by which the received oxygen may exit the tubing.

16 Claims, 10 Drawing Sheets

(56) References Cited

U.S. PATENT DOCUMENTS

| | | | |
|---|---|---|---|
| 6,110,139 | A | 8/2000 | Loubser |
| 6,312,647 | B1 | 11/2001 | Spears |
| 6,673,594 | B1 | 1/2004 | Owen et al. |
| 6,953,655 | B1 | 10/2005 | Hassanein et al. |
| 7,176,015 | B2 | 2/2007 | Alford et al. |
| 7,238,165 | B2 | 7/2007 | Vincent et al. |
| 7,338,461 | B2 | 3/2008 | Linde et al. |
| 7,811,808 | B2 | 10/2010 | van der Plaats et al. |
| 7,896,834 | B2 | 3/2011 | Smisson, III et al. |
| 7,985,536 | B2 | 7/2011 | Brasile |
| 8,057,419 | B2 | 11/2011 | Ellingboe et al. |
| 8,178,041 | B2 | 5/2012 | Thomas |
| 9,357,766 | B2 | 6/2016 | Steinman et al. |
| 9,357,767 | B2 | 6/2016 | Steinman et al. |
| 9,723,830 | B2 | 8/2017 | Steinman et al. |
| 2004/0170950 | A1 | 9/2004 | Prien |
| 2005/0147958 | A1 | 7/2005 | Hassanein et al. |
| 2005/0153271 | A1 | 7/2005 | Wenrich |
| 2006/0121439 | A1* | 6/2006 | Baker ................ A01N 1/0247 435/284.1 |
| 2006/0137522 | A1 | 6/2006 | Nishimura et al. |
| 2006/0154359 | A1 | 7/2006 | Hassanein et al. |
| 2009/0291486 | A1 | 11/2009 | Wenrich |
| 2010/0330547 | A1 | 12/2010 | Tempelman et al. |
| 2011/0076666 | A1* | 3/2011 | Brassil ............... A01N 1/0247 435/284.1 |
| 2011/0236875 | A1 | 9/2011 | Lee et al. |
| 2012/0143115 | A1 | 6/2012 | Muller-Spanka et al. |
| 2012/0178150 | A1 | 7/2012 | Tempelman et al. |
| 2014/0017657 | A1* | 1/2014 | Kravitz ............... A01N 1/0273 435/284.1 |
| 2014/0017659 | A1* | 1/2014 | Steinman ............ A01N 1/0247 435/284.1 |
| 2014/0017662 | A1* | 1/2014 | Kravitz ............... A01N 1/0247 435/284.1 |
| 2014/0017664 | A1* | 1/2014 | Kravitz ............... A01N 1/0273 435/284.1 |
| 2014/0017666 | A1* | 1/2014 | Steinman ............ A01N 1/0247 435/284.1 |
| 2015/0231322 | A1* | 8/2015 | Spearman ........... A61M 1/369 210/175 |
| 2015/0272111 | A1* | 10/2015 | Steinman ............ A01N 1/0247 435/284.1 |
| 2018/0310549 | A1* | 11/2018 | Alsberg .............. A01N 1/0273 |

FOREIGN PATENT DOCUMENTS

| | | | |
|---|---|---|---|
| JP | H04-099701 | A | 3/1992 |
| JP | H05-502060 | A | 4/1993 |
| JP | 2001516768 | A | 10/2001 |
| JP | 2015-527997 | A | 9/2015 |
| WO | 9106692 | A1 | 5/1991 |
| WO | 9915011 | A1 | 4/1999 |
| WO | 02089571 | A1 | 11/2002 |
| WO | 2007/107327 | A1 | 9/2007 |
| WO | 2010/087986 | A2 | 8/2010 |
| WO | 2012/170633 | A1 | 12/2012 |
| WO | 2013/068753 | A1 | 5/2013 |
| WO | 2018/201138 | A1 | 11/2018 |

OTHER PUBLICATIONS

Steinman. "BR-1120150004652" Publishing Date: Aug. 2017. Search of Brazilian National Institute of Industrial Property Ministry of Economy (machine translation). Searched Mar. 3, 2023. (Year: 2023).*

Apr. 27, 2022 Office Action issued in Chinese Patent Application No. 202080020240.1.

Aug. 25, 2021 International Preliminary Report on Patentability issued in International Patent Application No. PCT/US2020/021391.

Jun. 29, 2020 International Search Report issued in International Patent Application No. PCT/US2020/021391.

Jun. 29, 2020 Written Opinion issued in International Patent Application No. PCT/US2020/021391.

Jan. 13, 2015 International Preliminary Report on Patentability issued in International Patent Application No. PCT/US2013/049594.

Jul. 8, 2013 International Search Report issued in International Patent Application No. PCT/US2013/049594.

Jul. 8, 2013 Written Opinion issued in International Patent Application No. PCT/US2013/049594.

Jan. 5, 2016 Office Action issued in Chinese Patent Application No. 201380046882.9.

Feb. 21, 2017 Office Action issued in Japanese Application No. 2015-521697.

Jul. 27, 2017 Office Action issued in Chinese Patent Application No. 201380046882.9.

Apr. 2, 2018 Office Action issued in Chinese Patent Application No. 201380046882.9.

Sep. 11, 2018 Office Action issued in Japanese Application No. 2015-521697.

Feb. 19, 2019 Office Action issued in Brazilian Patent Application No. BR112015000465-2.

Dec. 28, 2022 Office Action issued in Chinese Patent Application No. 202080063466.X.

Dec. 7, 2023 Office Action issued in U.S. Appl. No. 17/015,443.

Jan. 2, 2024 Office Action issued in Chinese Patent Application No. 202080063466.X.

Jan. 16, 2024 Office Action issued in Japanese Patent Application No. 2021-555337.

Sep. 5, 2023 Office Action issued in Chinese Patent Application No. 202080063466.X.

Apr. 26, 2023 Office Action issued in U.S. Appl. No. 17/015,443.

M. W. Lim, "The history of extracorporeal oxygenators," Anaesthesia, 2006, 61, pp. 984-995. (Year: 2006).

Feb. 14, 2025 Decision to Grant issued in European Patent Application No. 20 797 237.3.

Aug. 27, 2024 Office Action issued in U.S. Appl. No. 17/015,443.

Aug. 27, 2024 Office Action issued in Japanese Patent Application No. 2021-555337.

May 7, 2024 Office Action issued in Japanese Patent Application No. 2022-516239.

Mar. 26, 2025 Notice of Allowance received in U.S. Appl. No. 17/015,443.

Jan. 13, 2025 Office Action issued in Indian Patent Application No. 202247013769.

Jan. 14, 2025 Office Action issued in Brazilian Patent Application No. 112022004154-3.

Mar. 6, 2025 Office Action issued in Brazilian Patent Applcation No. 112021017249-1.

Mar. 4, 2025 Office Action issued in Australian Patent Application No. 2020238826.

Mar. 18, 2025 Office Action issued in Japanese Patent Application No. 2022-516239.

Apr. 10, 2025 Decision to Grant issued in European Patent Application No. 20716293.4.

May 13, 2025 Decision to Grant issued in Japanese Patent Application No. 2021-555337.

May 16, 2025 Notice of Acceptance issued in Australian Patent Application No. 2020238826.

* cited by examiner

OXYGENATOR DEVICE

BACKGROUND

Related technical fields include organ or tissue perfusion apparatuses that are capable of sustaining and/or restoring viability of organs or tissue and preserving organs or tissue for diagnosis, treatment, storage, and/or transport. For convenience, the term "organ" as used herein should be understood to mean organ and/or tissue unless otherwise specified.

It is an objective of organ perfusion apparatuses to mimic the conditions of the human body such that the organ remains viable before being used for research, diagnosis, treatment, or transplantation. Often the organ must be stored and/or transported between facilities. A goal of sustaining and restoring organs during perfusion is to reduce ischemia and reperfusion injury. The increase in storage periods in a normal or near normal functioning state also provides certain advantages. For example, organs can be transported greater distances and there is increased time for testing, treatment, and evaluation of the organs.

Various organ perfusion apparatuses are known. U.S. Pat. Nos. 9,357,767; 9,357,766; and 9,723,830 disclose, for example, a perfusion apparatus that employs a disposable perfusion circuit within which the organ may be stored during perfusion. This circuit comprises a basin that may serve as a receptacle for an organ cradle on which the organ may be placed and for a perfusate bath that may be formed around the organ. Inner and outer lids may be used to close the basin during perfusion, and the basin may fit within a coolant container so that both the perfusate bath and the organ are brought to hypothermic temperatures. The contents of these prior patents are incorporated by reference herein in their entirety.

SUMMARY

Although the use of hypothermic temperatures during transportation and perfusion greatly improves organ preservation by decreasing oxygen demands and metabolic activity of the organ, it does not completely eliminate them. A corresponding lack of oxygen can drive the cells of the organ to anaerobic activity, which causes a buildup of lactate and mitochondrial uncoupling and depleted adenosine triphosphate ("ATP") stores, and thereby leads to the release of toxic molecules such as radical oxygen species, inflammatory cytokines, and lactate. These toxic molecules and mitochondrial activity increase the production of reactive oxygen molecules, which may in turn lead to adverse ischemia and reperfusion injury.

Given that a lack of oxygen drives the cells to anaerobic activity and worsens ischemia and reperfusion injury, there has been great interest in the benefits associated with increasing oxygen to a hypothermic perfused organ by, say, introducing additional oxygen into the perfusate solution. U.S. patent application Ser. No. 13/545,514, the entire contents of which are hereby incorporated by reference, discloses an oxygen generator or concentrator that preferably produces oxygen in real time to provide oxygenation to the perfusate, for example.

However, there are at least two difficulties associated with prior oxygenation devices and methods. The first is the amount of time required to adequately oxygenate the perfusate solution. Time during organ transplantation is at a premium, so an oxygenator device should be able to rapidly oxygenate the perfusate solution. Further, hospitals and clinics may have also acquired or purchased a substantial amount of disposables to be used during perfusion, and may be hesitant to discard these likely expensive disposables to oxygenate the perfusate solution. There is thus also a need for an oxygenator device that works with existing equipment and disposables to oxygenate the perfusate solution.

Thus disclosed herein is an oxygenator device for oxygenating a perfusate solution to be perfused through an organ or tissue. This device may comprise an inlet configured to receive oxygen from an oxygen supply, and it may also comprise tubing connected to the inlet, the tubing including a plurality of holes by which the received oxygen may exit the tubing.

In combination with any of the above or below features, the oxygenator device may also comprise a top portion from which the inlet extends, and it may further include a plurality of holders extending below the top portion so as to secure the tubing below the top portion.

In combination with any of the above or below features, each of the plurality of holders may also include (i) a vertical portion extending substantially perpendicular to the top portion and (ii) an angled portion extending at an outward angle relative to the vertical portion. The tubing may be secured by the angled portions of the plurality of holders.

In combination with any of the above or below features, the plurality of holders may secure the tubing in a loop having a circumference sufficient to encircle the organ or tissue in use, and a majority of this loop may be substantially parallel to a virtual plane formed by the top portion.

In combination with any of the above or below features, the oxygenator device may be configured to be attached to an organ perfusion circuit, and a top portion of the oxygenator device, from which the inlet extends, may constitute a lid for a basin of the organ perfusion circuit that is configured to hold the organ or tissue during perfusion.

In combination with any of the above or below features, the tubing may be fixed below the top portion so that, when the oxygenator device is placed on the basin, the tubing and the plurality of holes therein may be submerged in a bath of the perfusate solution in the basin.

In combination with any of the above or below features, the tubing may be secured in position by a plurality of holders so that, when the oxygenator device is placed on the basin, the tubing does not interfere with an organ cradle locatable within the basin.

In combination with any of the above or below features, the oxygenator device may further comprise a hydrophobic vent in the top portion, the vent being configured to limit pressure increase within the basin when the oxygenator device is placed on the basin and oxygen flows from the plurality of holes in the tubing to the perfusate solution.

In combination with any of the above or below features, the holes may be arranged in a plurality of groupings spaced apart along a length of the tubing.

In combination with any of the above or below features, each of the groupings may comprise a plurality of the holes spaced apart around a circumference of the tubing.

In combination with any of the above or below features, each pair of the plurality of groupings may be spaced apart by 34.79 mm of the tubing, and an average diameter of the plurality of holes may be between 0.10 mm and 0.18 mm.

Also disclosed herein is a method of using the oxygenator device in accordance with any of the above features. This method may include placing the oxygenator device on a basin of an organ perfusion circuit so that the tubing and the holes therein are submerged within a bath of the perfusate solution within the basin; connecting the inlet of the oxygenator device to an oxygen supply; and administering oxygen from the oxygen supply, through the inlet, through the holes in the tubing, and into the perfusate bath so as to increase oxygen concentration of the perfusate solution constituting the bath.

The method may also include a step of administering the oxygen from the oxygen source at a rate of about 10 liters per minute for at least 10 minutes.

It may further include, prior to the placing step, removing a lid of the basin. The placing step may thus replace the lid of the basin with the oxygenator device.

The method may yet further include steps of discontinuing administration of the oxygen from the oxygen supply, and then placing the organ or tissue in the basin of the organ perfusion circuit.

And the oxygen may alternatively be administered while the organ or tissue is being perfused in the organ perfusion circuit.

These and other aspects of the present disclosure will be described with reference to the attached drawings and following detailed description.

DETAILED DESCRIPTION OF EMBODIMENTS

Figure 1:
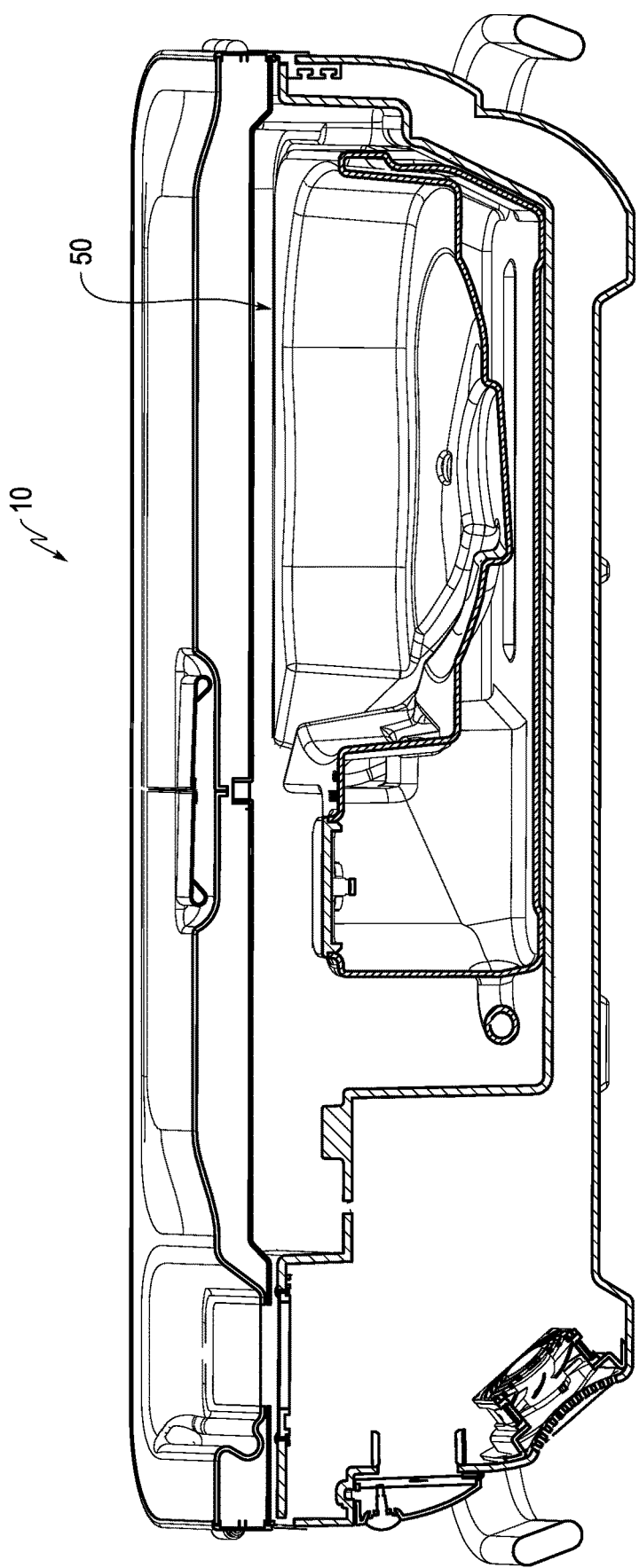
FIG. 1 is a cross-sectional view of an organ perfusion apparatus according to one or more embodiments of the disclosure.
Figure 2:
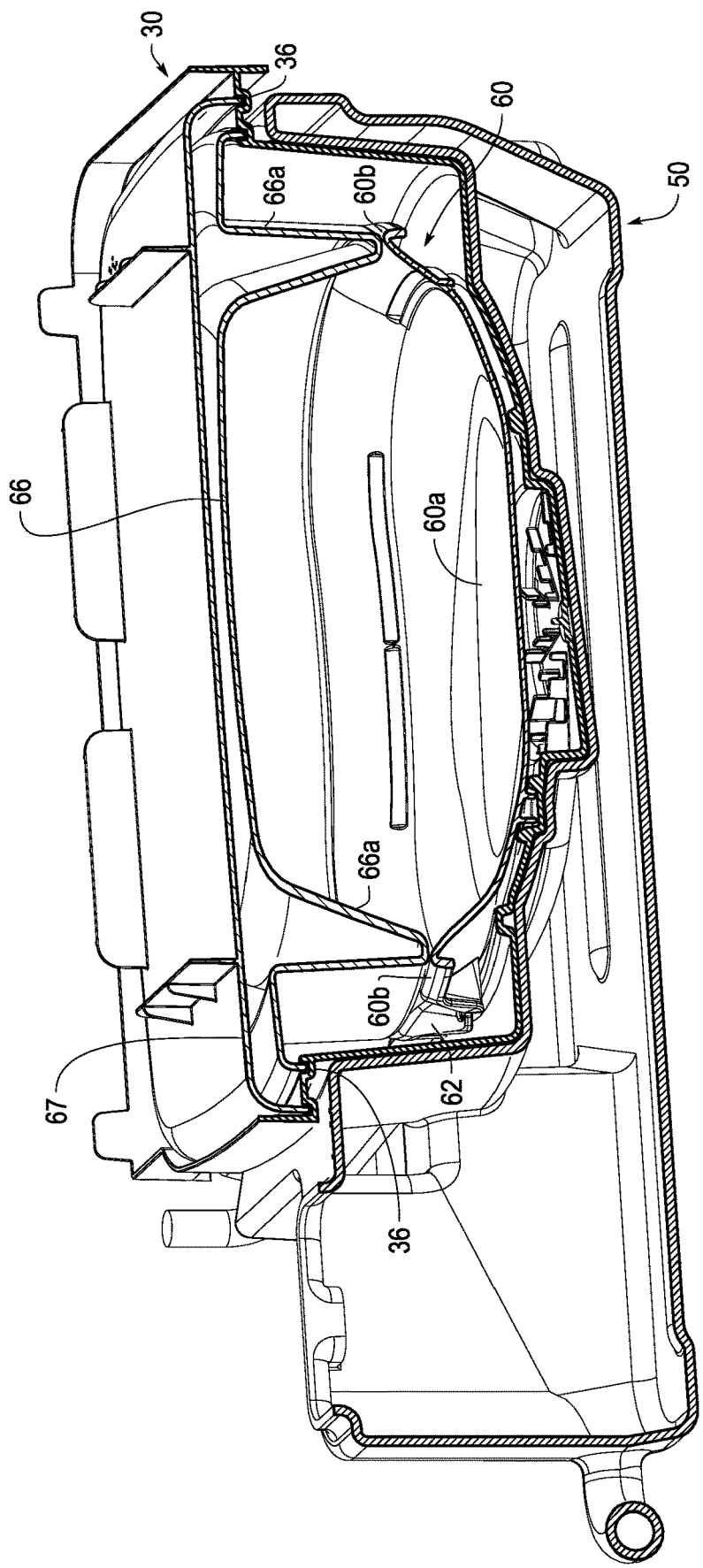
FIG. 2 is a cross-sectional view of the combined coolant container, basin, and cradle of the organ perfusion apparatus of FIG. 1.

FIGS. 1 and 2 show an exemplary perfusion apparatus 10 for an organ. The organ may preferably be a liver, kidney, heart, lung, or intestine, but it may be any human or animal, natural or engineered, healthy, injured, or diseased organ or tissue. The apparatus 10 may include a basin 30 (see FIG. 2) in which the organ may be placed. The basin 30 may hold a removable cradle 60, which may preferably include a surface 60a on which the organ may be disposed when the organ is in the apparatus 10. The basin 30 and/or the cradle 60 may preferably be configured to allow a perfusate bath of perfusate solution such as VASOSOL® to be contained around the organ.

The basin 30 may preferably be disposed within an insulating coolant container 50 that may contain cold materials such as ice, ice water, brine, or the like. Coolant container 50 may be permanently or removably attached to, or an integral, monolithic part of, apparatus 10. Thus, in use, the organ may be disposed within the cradle 60, which may be disposed within the basin 30, which may be disposed within the coolant container 50, as shown in FIG. 2. The arrangement of the coolant container 50, basin 30, and cradle 60 preferably provides a configuration that provides cooling for the organ without the contents of coolant container 50 contacting the organ or the cradle 60. Although the coolant container 50 is described herein as containing ice or ice water, any suitable cooling medium can be used.

As further shown in FIG. 2, an inner lid 66 and an outer lid 67 may be provided on an upper surface of the basin 30. The inner lid 66 may be sized to come into close proximity to the perimeter top surface of the cradle 60 to help maintain stability of the organ in the event of mechanical impact and shock during transport. More specifically, the inner lid 66 may have a downwardly protruding extension 66a that matches a circumferential shape of a peripheral ridge 60b of the cradle 60 and is configured to contact the peripheral ridge 60b and help hold the cradle 60 in position. The lids 66 and 67 may create a substantially fluid-tight seal with the basin 30, and they can prevent contamination. The lids 66 and 67 may also provide for a redundant airtight seal should the seal from either lid 66 or 67 fail. Both the inner lid 66 and the outer lid 67 may preferably contain an air vent, e.g., a porous hydrophobic membrane, that allows for gas transfer in order to maintain pressure equilibrium.

Preferably, all components of the apparatus 10 that come into contact with perfusate solution and/or the organ are disposable and/or easily replaced. These components may include the basin 30, the organ cradle 60, and the lids 66 and 67, which may constitute parts of a disposable organ perfusion circuit. In use, this disposable organ perfusion circuit may be placed within the non-disposable portion of the apparatus 10, and the organ may be placed on the organ cradle 60 within the basin 30. Because of the presence of the coolant container 50, both the organ and the perfusate bath within the basin 30 are subjected to hypothermic temperatures. The perfusate solution may then be circulated through the disposable perfusion circuit and the organ.

Figure 3:
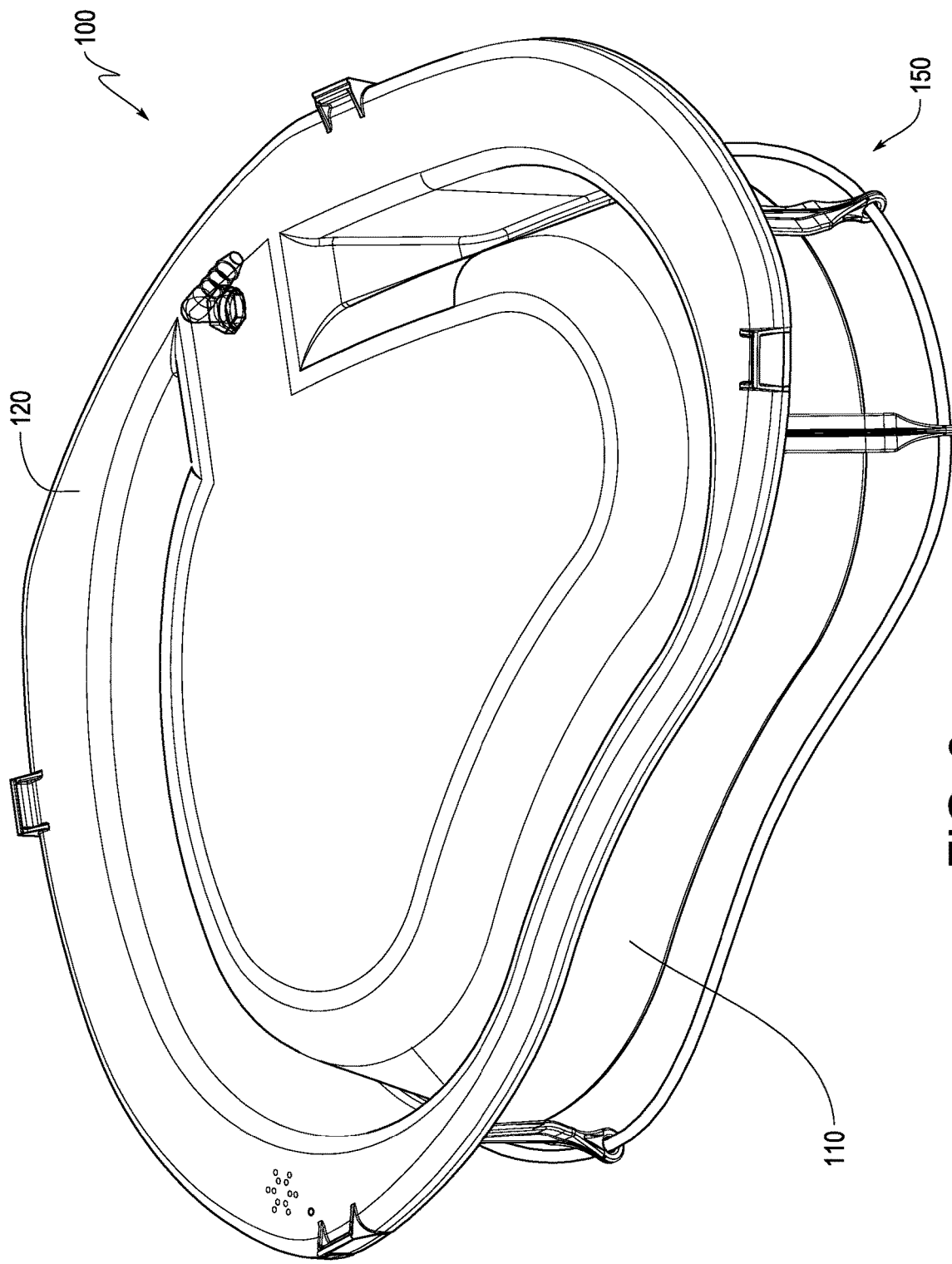
FIG. 3 is a top perspective view of an oxygenator device according to one or more embodiments of the disclosure.
Figure 4:
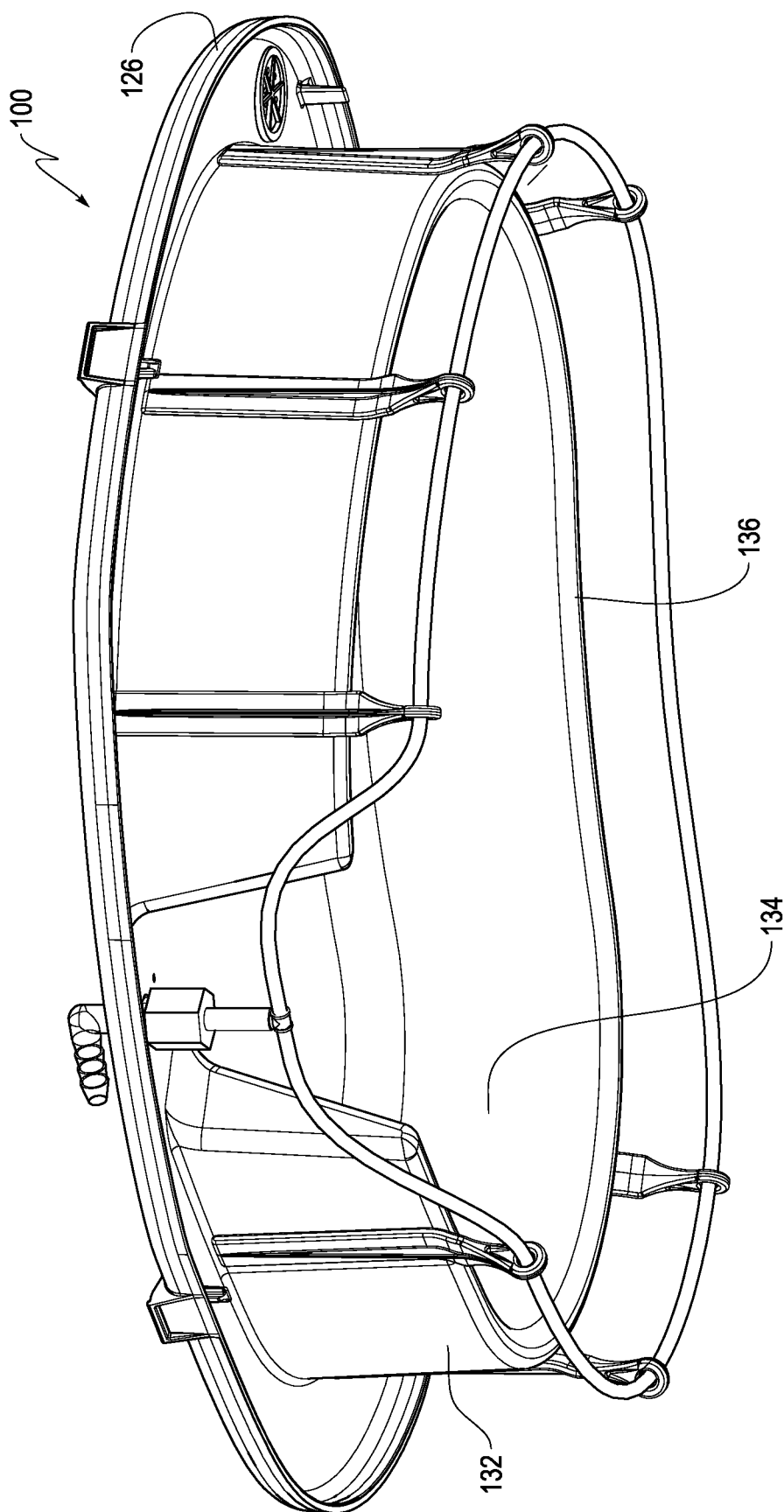
FIG. 4 is a bottom perspective view of the oxygenator device of FIG. 3.
Figure 5:
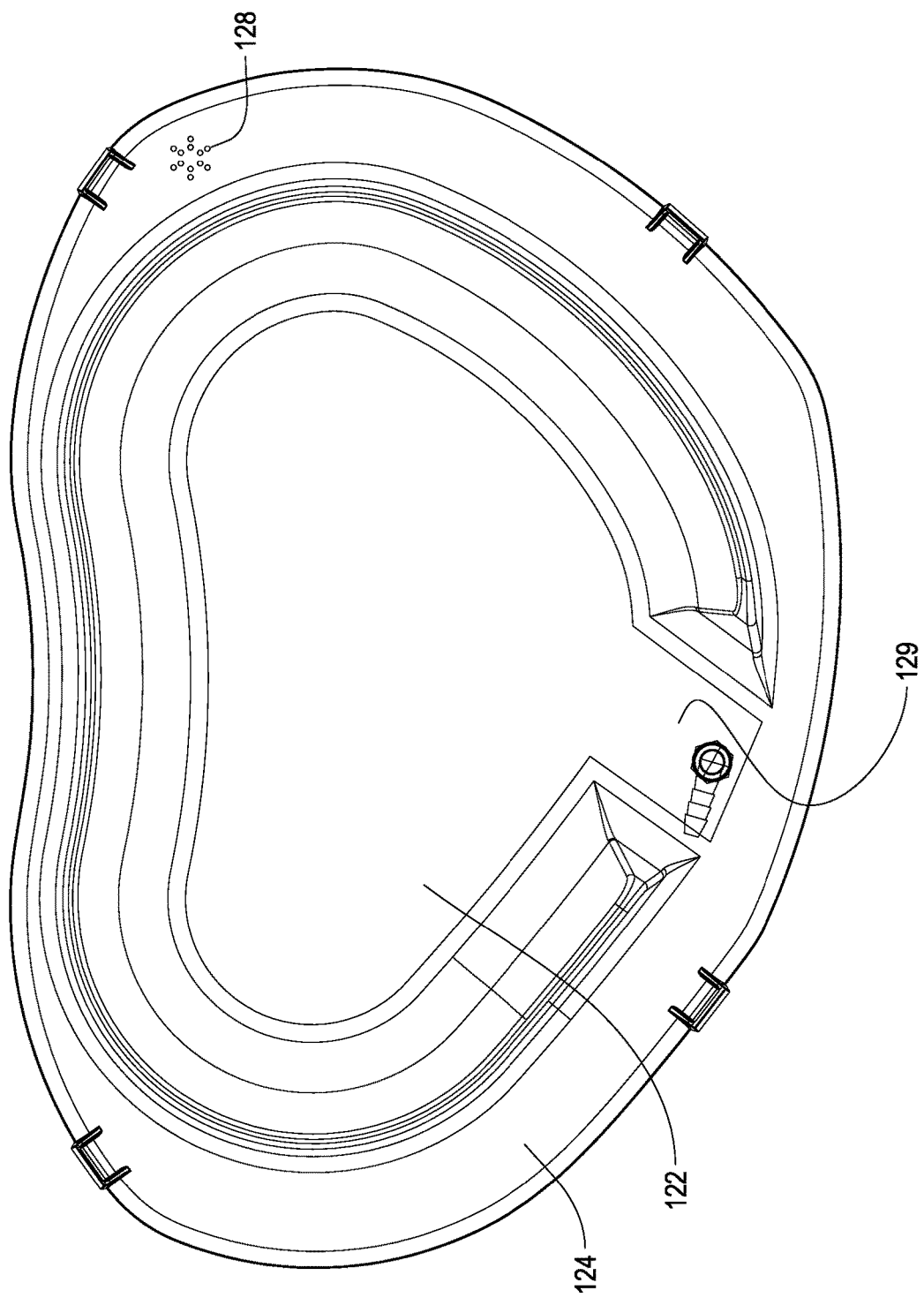
FIG. 5 is a top plan view of the oxygenator device of FIG. 3.
Figure 6:
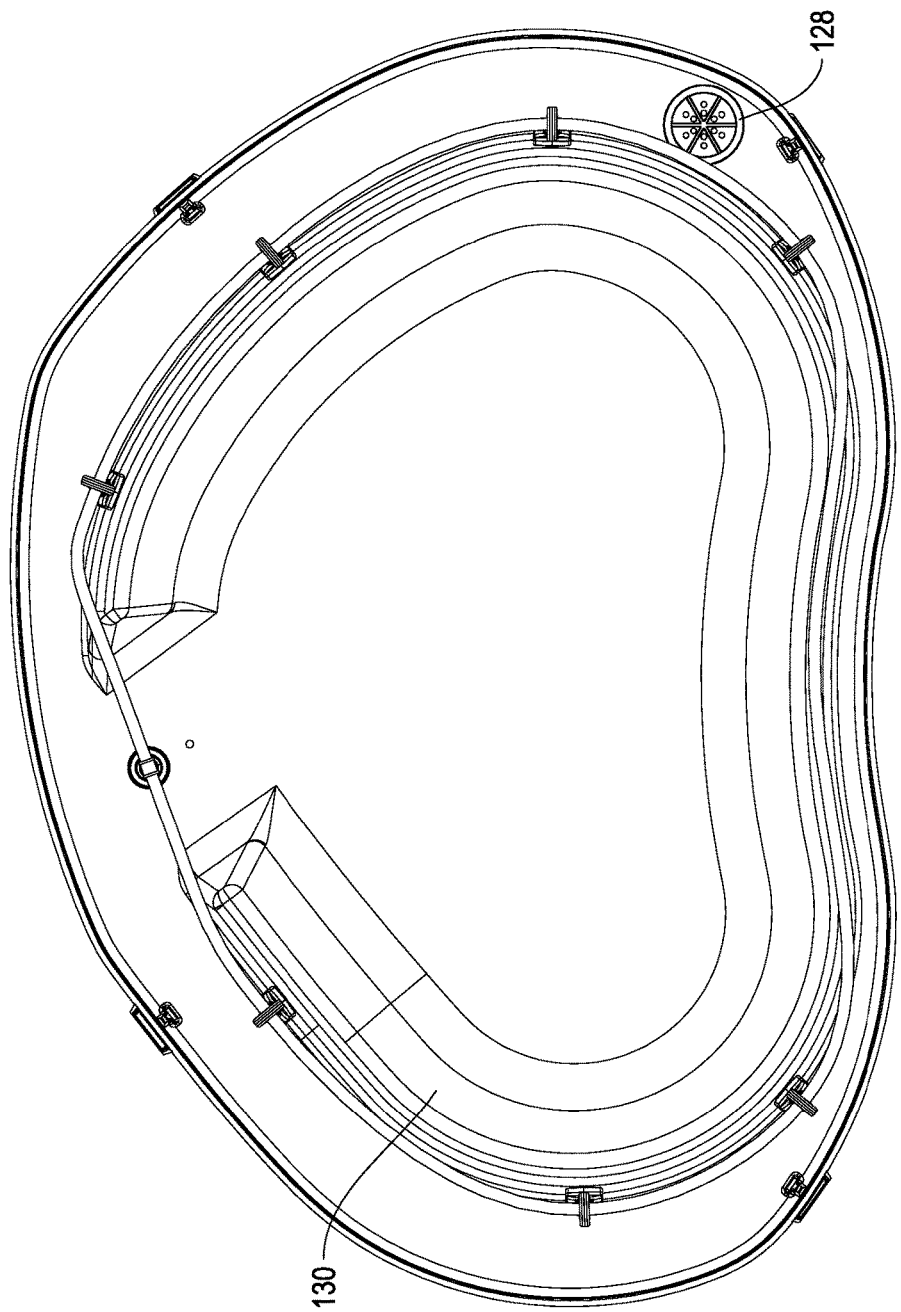
FIG. 6 is a bottom plan view of the oxygenator device of FIG. 3.

FIGS. 3 and 4 show an oxygenator device 100 in accordance with one or more aspects of the present disclosure. The device 100 may be designed to work with the perfusion apparatus 10 to increase the oxygen concentration of the perfusate bath within the basin 30. This device 100 may generally be constituted by a main body 110 and oxygenation components 150. The main body 110 may in turn include a top portion 120 including, as shown in FIG. 5, radially inner and outer portions 122 and 124. The main body 110 may also include, as shown in FIG. 6, a bottom portion 130 projecting downward from the top portion 120. The main body 110 may be formed, for example, from clear polycarbonate plastic resin.

Figure 7:
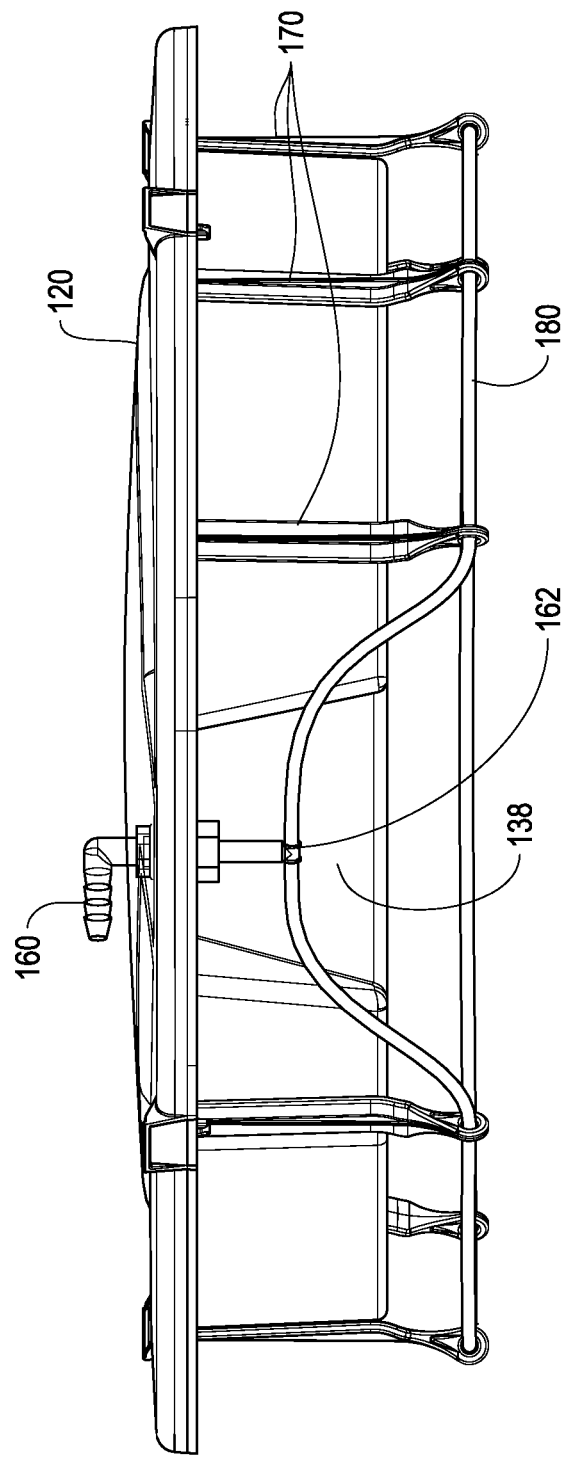
FIG. 7 is a side elevation view of the oxygenator device of FIG. 3.
Figure 8:
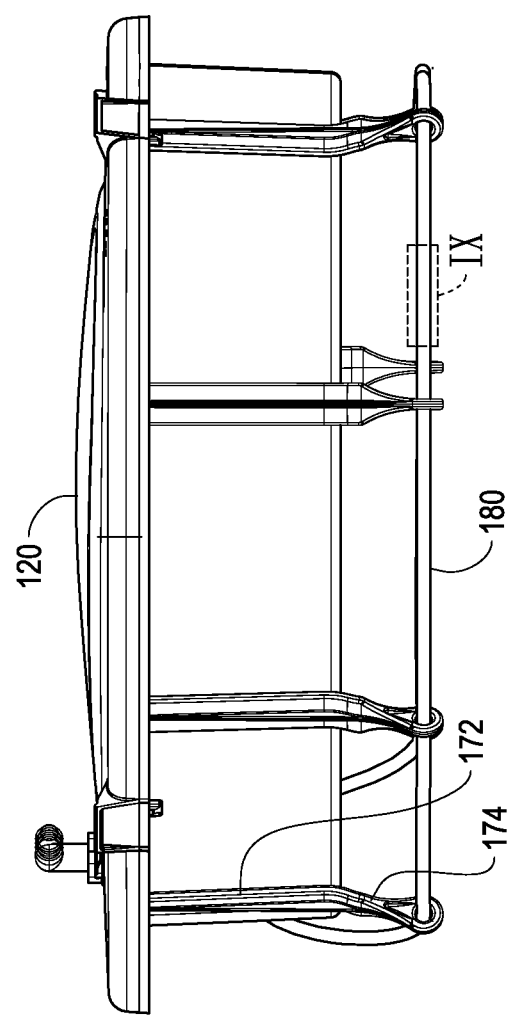
FIG. 8 is another side elevation view of the oxygenator device of FIG. 3.

The top portion 120 may be, like the inner lid 66, sized to correspond to the basin 30. More specifically, a lower lip 126 (see FIG. 4) of the radially outer portion 124 of the top portion 120 may be sized so as to be received by an indentation 36 (see FIG. 2) in an upper surface of the basin 30 and thereby allow the oxygenator device 100 to constitute a lid for that basin in place of the inner lid 66. Latches (not shown) on the basin 30 may be used to lock the oxygenator device 100 in place relative to the basin 30. As shown in FIGS. 7 and 8, the top portion 120 may be substantially planar. That is, although the surface of at least one of the radially inner and outer portions 122 and 124 may be slightly inclined, the overall shape of the top portion 120 forms a virtual plane projecting into the pages of FIGS. 7 and 8. For example, the outer portion 124 may be flat, whereas the inner portion 122 may be convex outward. Also provided within the top portion 120 may be a vent 128 (see FIGS. 5 and 6). Like the air vents of the lids 66 and 67, the vent 128 may include a porous hydrophobic membrane, which allows for gas transfer in order to maintain pressure equilibrium. More specifically, the membrane of the vent 128 may be an acrylic copolymer treated to render it hydrophobic and oleophobic, and the membrane may be attached and bonded to a non-woven nylon substrate. The membrane itself may have an average porosity of 0.45 microns, and it may repel and be resistant to oil, water, and organic solvents and be non-wettable by most low-surface-tension liquids. This stands in contrast to, say, a hydrophilic membrane that has a tendency to mix with or be wettable by such liquids. Around the perimeter of the vent 128 may be provided an adhesive to secure the vent 128 to the remainder of the top portion 120 and thereby ensure that it remains attached thereto with a tight seal.

The bottom portion 130 may be formed in the space between the radially inner and outer portions 122 and 124 of the top portion 120, and it may have a substantially triangular shape in cross-section. More specifically, a radially outer wall 132 (see FIG. 4) of the bottom portion 130 may extend downward substantially perpendicular to the virtual plane of the top portion 120, and a radially inner wall 134 of the bottom portion 130 may extend downward from the top portion 120 at an angle inclined relative to the outer wall 132. The walls 132 and 134 may meet at a vertex 136, thereby ensuring that the main body 110 is able to create a substantially fluid-tight seal with the basin 30 and thereby prevent contamination. Finally, the bottom portion 130 (and particularly the vertex 136) may, like the downwardly protruding extension 66a of the inner lid 66, also match the circumferential shape of the peripheral ridge 60b of the cradle 60, and it may thus likewise be configured to contact that peripheral ridge and help hold the cradle 60 and any organ thereon in position.

The oxygenation components 150 may in turn include, as shown in FIG. 7, an oxygen inlet 160, a T-fitting 162, holders 170, and tubing 180. The oxygen inlet 160 may be an oxygen barb projecting from a bridge portion 129 (see FIG. 5) that connects the radially inner and outer portions 122 and 124 of the top portion 120. The oxygen inlet 160 may be angled substantially perpendicular to the virtual plane of the top portion 120 to facilitate ease of use and to reduce the risk of kinking of the tube delivering oxygen to the inlet. The T-fitting 162 may in turn be fluidly connected to the oxygen inlet 160, and it may be formed below the bridge portion 129 in a gap 138 formed in the bottom portion 130.

The tubing 180 may be fluidly connected to the T-fitting 162, and it may be secured in position by the plurality of holders 170. As shown in FIG. 8, each of these holders 170 may include an upper, vertical portion 172 secured to the bottom portion 130 of the main body 110 and projecting from the top portion 120 in a direction substantially perpendicular to the virtual vertical plane of the top portion 120. The holders 170 may secure the tubing 180 below the bottom portion 130, and each of the holders 170 may also include an angled portion 174 that is angled outward relative to the vertical portion 172. The angled portion 174 may be angled relative to the vertical portion 172 by, say, 2.5 degrees, although other angles are possible. The angled portion 174 of each of the holders 170 may include a hole through which the tubing 180 may pass. As discussed below, angling the angled portions 174 relative to the vertical portions 172 may help ensure that neither the holders 170 nor the tubing 180 interferes in use with the organ cradle 60, any organ or vasculature thereon, or cannula that may be disposed within the basin 30. The rounded ends of the angled portions 174, at which the holes are located, may also ensure that there is no crashing or interference with the basin 30 during use.

Figures 9, 10, 11:
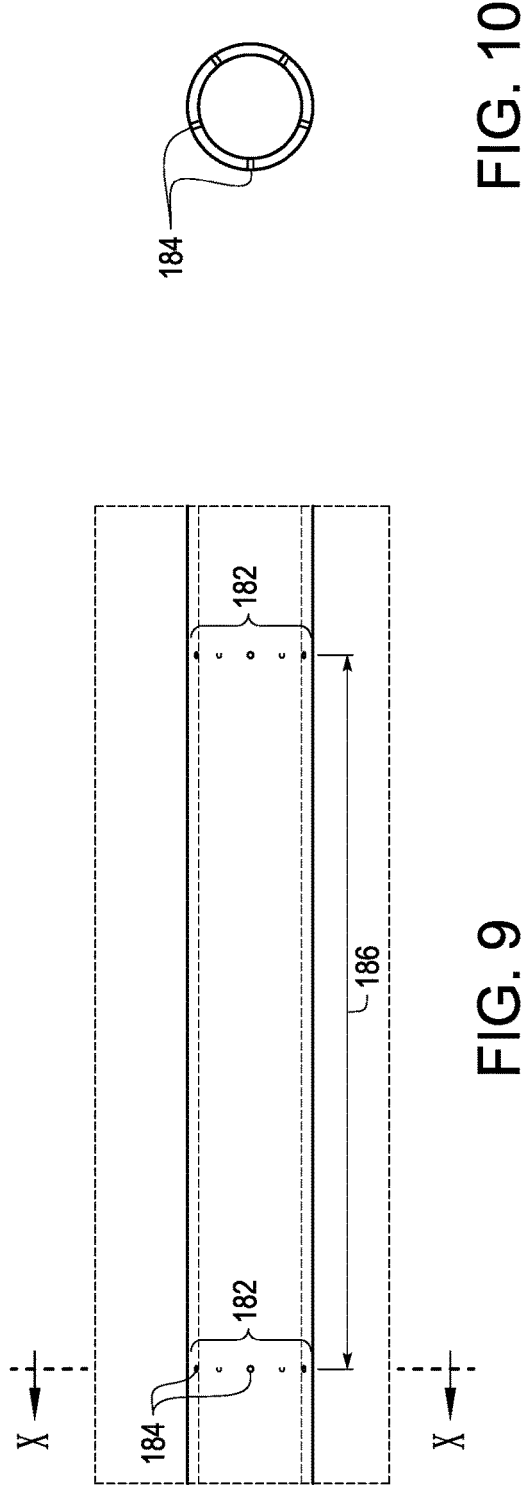
FIG. 9 is an enlarged view of a portion IX of the tubing shown in FIG. 8.
FIG. 10 is a cross-sectional view of the tubing taken along line X-X in FIG. 9.
FIG. 11 shows a process of using the oxygenator device of FIG. 3.

The tubing 180 may be formed of aromatic polyether-based polyurethane, and it may be of sufficient length to encircle the bottom portion 130 and thus to encircle a perfused organ when the oxygenator device 100 serves as the lid for the basin 30. Preferably, the total length of the tubing 180 may be equal to or about 1,054.10 mm, although other lengths are possible. FIG. 9 shows an enlarged view of the portion IX of the tubing 180 shown in FIG. 8, and as shown in this Figure, the tubing 180 may include a plurality of groupings 182 of holes 184 that may be spaced apart along the length of the tubing 180 by a distance 186. Preferably, the distance 186 may be equal to or about 34.79 mm, although other distances are possible. 24 groupings 182 may be formed in the tubing 180, and as shown in FIG. 10, which shows a cross-section of the tubing 180 at one of the groupings 182, each grouping may include 5 holes 184 equally spaced around the circumference of the tubing 180. The tubing 180 may thus include a total of 120 holes 184. Each of the holes 184 may be formed in the tubing 180 by way of laser ablation. And each hole 184 may have a diameter of 0.10 mm to 0.18 mm, which has been shown to be well within the capability of the laser ablation process and repeatable. Instead of the tubing 180, hollow fiber filters may be used to provide oxygen to the perfusate solution. Hollow fiber filters may prevent bubbling of the perfusate solution during the oxygenation process. But if the perfusate solution is not whole blood, this potential difference may be insufficient to justify the substantial increase in cost of hollow fiber filters relative to the tubing 180.

The above-described arrangement of the holes 184, and particularly their number and diameter, achieves a sufficiently short time to "bubble" and therefore saturate the perfusate solution of the perfusate bath with oxygen while maintaining a suitable cost. Preferably, at an oxygen flow rate of, say, 10 liters per minute, the holes 184 ensure that the perfusate solution of the bath will be saturated within a timeframe of 10-15 minutes, which is acceptable for most clinics as surgical procedures taking place concurrently may take substantially longer. Other numbers of holes 184 and other sizes of those holes are possible; however, various considerations should be taken into account. More holes 184 of the same diameter, for example, may reduce the time required to fully saturate the perfusate solution. But cost of the tubing 180 is directly proportional to the number of holes 184, so increasing their number may result in increased cost of the tubing. Substantially less holes 184, on the other hand, may unsatisfactorily increase the time required to saturate the perfusate solution of the bath.

Other arrangements of the holes 184 are also possible. They could be positioned linearly along the length of the tubing 180, for example. However, the above-described arrangement with the groupings 182, in which five holes 184 are spaced around the circumference of the tubing 180, helps ensure that at least most of the holes 184 are placed below the surface of the perfusate in use. Equally spacing the groupings 182 by the distance 186 across the length of the tubing 182 may also help ensure that most of the perfusate solution is evenly exposed to oxygen gas, thereby preventing one region from being under-concentrated.

Figure 12:
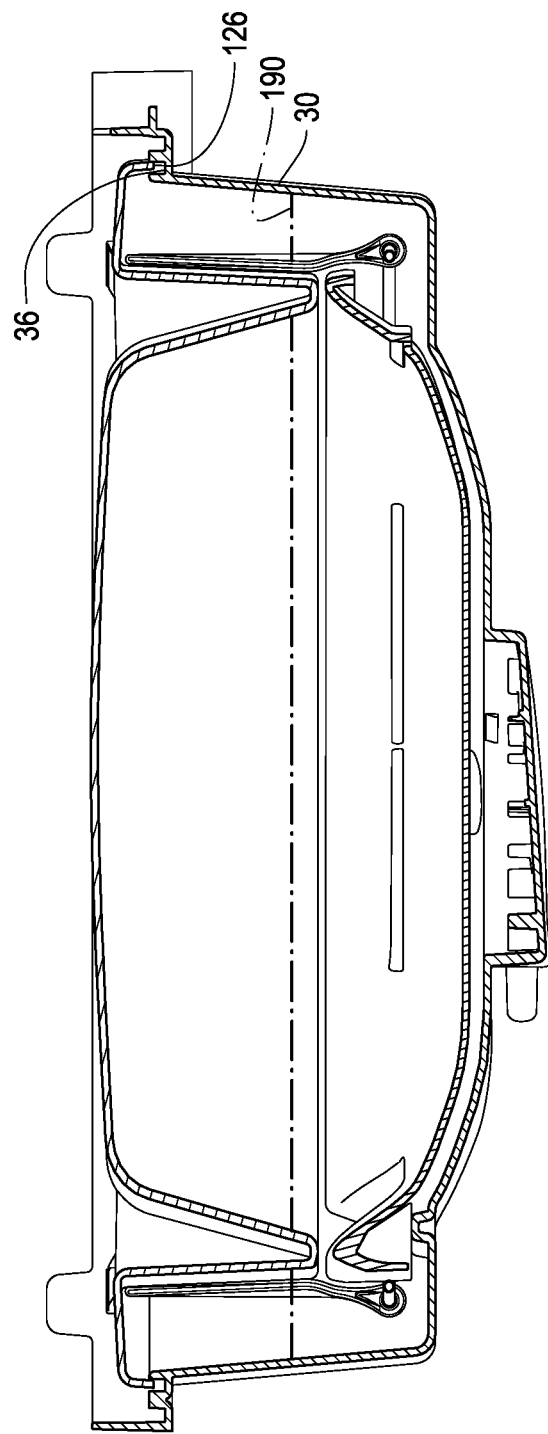
FIG. 12 is a cross-sectional view of the oxygenator device of FIG. 3 placed on a basin of an organ perfusion circuit.

FIG. 11 shows a method by which the oxygenator device 100 may be used with a perfusion apparatus, e.g., the perfusion apparatus 10, to increase the dissolved oxygen content in the perfusate solution constituting a perfusate bath. In a first step 210, the oxygenator device 100 may be placed on the basin 30. This arrangement is shown by cross-section in FIG. 12. As shown in this Figure, the lower lip 126 of the oxygenator device 100 may be sized so as to correspond to the depression 36 in the top surface of the basin 30. The holders 170 may also secure the tubing 180 and the holes 184 therein low enough within the basin 30 to be submerged within the perfusate bath, a possible level of which is shown by 190 in FIG. 12. And also by virtue of the angled portions 174 of the holders 170, the tubing 180 may be located outside so as not to interfere with the organ cradle 60, any organ or vasculature thereon, or any cannula in the assembled position shown in FIG. 12. The oxygenator device 100 may be secured to the basin 30 by way of the aforementioned latches.

In a next step 220 the oxygenator device 100 may be connected to an external oxygen source. Other than preferably providing regulated, medical-grade oxygen, the oxygen source is not particularly limited. It may be, for example, an oxygen cylinder or a wall valve in a hospital or clinic setting. To connect the oxygenator device 100 and the oxygen source, a user or users of the device 100 may attach one end of an extension tube to the oxygen inlet 160 and another end of that tube to the oxygen source.

Following step 220, oxygen may be administered in a step 230. Preferably, oxygen may be administered from the oxygen source at a rate at or about 10 liters per minute for at least 10 minutes, more preferably for at least 15 minutes, and even more preferably for at least 20 minutes. Other rates of oxygen flow are possible, however. For example, the oxygen could be administered from the oxygen source at a rate of 1, 2, or 3 liters per minute. But this may unacceptably lengthen the period of time required to fully saturate the perfusate solution of the perfusate bath. On the other hand, oxygen flow rates up to 20 liters per minute or more are conceived. However, flow rates greater than 20 liters per minute may create a risk of high back pressure on the connections between the tubing 180 and the T-fitting 162, which could prevent the perfusate bath from being fully saturated with oxygen due to leaks caused by the high pressure. Administering oxygen at the above preferred rate for the preferred duration may result in dissolved oxygen levels within the perfusate solution of 600-800 mmHg, which is believed to be desirable for perfusion of the organ. Despite the additional oxygen introduced into the basin 30 by way of the tubing 180 and the holes 184 therein, the vent 128 may prevent substantial increases in pressure of the atmosphere within the basin 30 and above the perfusate bath by venting most of the introduced oxygen to atmosphere. Indeed, the increase in atmosphere pressure within the basin 30 may be less than 5 mmHg. Once administration of oxygen is discontinued, the pressure within the basin 30 may equilibrate to that of the external atmosphere due to the vent 128.

Once desirable oxygenation levels have been reached, the oxygen administration may be discontinued and the oxygenator device 100 may be removed from the basin 30. Because the oxygenated perfusate is then open to atmosphere, the inner lid 66 may then preferably be placed on the basin 30 as soon as possible. The organ may then be placed within the basin 30 and perfused with the oxygenated perfusate solution. It is also conceivable that, once the administration of oxygen has been discontinued, there may be some delay in placing the organ within the basin 30 and beginning perfusion. It may therefore be necessary to oxygenate the perfusate solution again after a period of time so that the desirable oxygenation level can be maintained. Preferably this re-administration occurs prior to removal of the oxygenator device 100 from the basin 30, as the device's sterility may become compromised once removed from the basin.

The process 200 shown in FIG. 11 thus provides a means by which to pre-charge with oxygen a perfusate solution prior to placement of an organ within the perfusion circuit and subsequent perfusion of that organ. However, various modifications are envisioned. For example, the oxygenator device 100 may not be removed from the basin 30 once pre-charging is complete, and it could thus serve as the lid of the basin during perfusion of the organ. The oxygenator device 100 could also continue to oxygenate the perfusate during perfusion and/or transport of the organ. This oxygenation during perfusion could help maintain elevated oxygen levels in the perfusate throughout transport. Of course, a portable oxygen source would likely be beneficial for this modification. The step 210 of the process 200 may also be preceded by steps 205 and 207. In step 205, following priming and cooling of the perfusion circuit, the inner lid 66 of the perfusion circuit may be removed to make space for the oxygenator device 100. And in step 207, the perfusate solution may be decanted into the basin 30 so as to form the perfusate bath.

As explained above, the oxygenator device 100 thus provides a mechanism by which to rapidly oxygenate a perfusate solution, thereby providing the above-described benefits of oxygen while avoiding the hazards associated with delays in the transplantation process. It also works with existing perfusion circuits, ensuring that these costly disposables need not be replaced by a clinic or hospital to obtain the benefits of oxygenation.

What has been described and illustrated herein are embodiments of the invention along with some variations. The terms, descriptions and figures used herein are set forth by way of illustration only and are not meant as limitations. Those skilled in the art will recognize that many variations are possible within the spirit and scope of the invention.

What is claimed is:

1. A method of oxygenating a perfusate solution to be perfused through an organ or tissue, the method comprising:
   removing a lid of a basin of an organ perfusion circuit;
   replacing the lid of the basin with an oxygenator device by placing the oxygenator device on the basin so that tubing of the oxygenator device and a plurality of holes in the tubing are submerged within a bath of the perfusate solution within the basin, the tubing also being connected to an inlet of the oxygenator device;
   connecting the inlet of the oxygenator device to an oxygen supply; and
   administering oxygen from the oxygen supply, through the inlet, through the holes in the tubing, and into the perfusate bath so as to increase oxygen concentration of the perfusate solution constituting the bath.

2. The method of claim 1, further comprising administering the oxygen from the oxygen supply at a rate of about 10 liters per minute for at least 10 minutes.

3. The method of claim 1, further comprising:
   discontinuing administration of the oxygen from the oxygen supply;
   removing the oxygenator device from the basin; and
   then placing the organ or tissue in the basin of the organ perfusion circuit.

4. The method of claim 3, further comprising replacing the lid on the basin once the organ or tissue is placed in the basin.

5. The method of claim 1, wherein the oxygen is administered while the organ or tissue is being perfused in the organ perfusion circuit.

6. The method of claim 1, wherein the basin is disposed within an insulating coolant container of the organ perfusion circuit.

7. The method of claim 1, wherein the oxygenator device comprises:
a top portion from which the inlet extends; and
a plurality of holders extending below the top portion so as to secure the tubing below the top portion.

8. The method of claim 7, wherein:
each of the plurality of holders includes (i) a vertical portion extending substantially perpendicular to the top portion and (ii) an angled portion extending at an outward angle relative to the vertical portion; and
the tubing is secured by the angled portions of the plurality of holders.

9. The method of claim 8, wherein:
the plurality of holders secure the tube in a loop having a circumference sufficient to encircle the organ or tissue in use; and
a majority of the loop is substantially parallel to a virtual plane formed by the top portion.

10. The method of claim 1, wherein
a top portion of the oxygenator device, from which the inlet extends, constitutes another lid for the basin of the organ perfusion circuit.

11. The method of claim 10, wherein
the tubing is fixed below the top portion so that, when the oxygenator device is placed on the basin, the tubing and the plurality of holes therein are submerged in the bath of the perfusate solution in the basin.

12. The method of claim 11, wherein
the tubing is secured in position by a plurality of holders so that, when the oxygenator device is placed on the basin, the tubing does not interfere with an organ cradle locatable within the basin.

13. The method of claim 12, further comprising a hydrophobic vent in the top portion, the vent being configured to limit pressure increase within the basin when the oxygenator device is placed on the basin and oxygen flows from the plurality of holes in the tubing to the perfusate solution.

14. The method of claim 1, wherein the holes are arranged in a plurality of groupings spaced apart along a length of the tubing.

15. The method of claim 14, wherein each of the groupings comprises a plurality of the holes spaced apart around a circumference of the tubing.

16. The method of claim 15, wherein:
each pair of the plurality of groupings are spaced apart by about 34.79 mm of the tubing; and
an average diameter of the plurality of holes is between 0.10 mm and 0.18 mm.

* * * * *